US011320450B2

(12) United States Patent
Ikeuchi

(10) Patent No.: US 11,320,450 B2
(45) Date of Patent: May 3, 2022

(54) METHOD FOR ESTIMATING ATTACHMENT POSTURE OF INERTIAL SENSOR

(71) Applicant: Honda Motor Co.,Ltd., Tokyo (JP)

(72) Inventor: Yasushi Ikeuchi, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 232 days.

(21) Appl. No.: 16/810,869

(22) Filed: Mar. 6, 2020

(65) Prior Publication Data

US 2020/0292573 A1 Sep. 17, 2020

(30) Foreign Application Priority Data

Mar. 11, 2019 (JP) .............................. JP2019-043719

(51) Int. Cl.
| | |
|---|---|
| A61B 5/11 | (2006.01) |
| G01P 15/02 | (2013.01) |
| G01P 15/16 | (2013.01) |
| G01P 15/18 | (2013.01) |
| G01P 15/08 | (2006.01) |

(52) U.S. Cl.
CPC ................ *G01P 15/02* (2013.01); *A61B 5/11* (2013.01); *A61B 5/1116* (2013.01); *G01P 15/16* (2013.01); *G01P 15/18* (2013.01); *G01P 2015/084* (2013.01)

(58) Field of Classification Search
CPC .......... G01P 15/02; G01P 15/16; G01P 15/18; G01P 2015/08; A61B 5/11; A61B 5/1116
See application file for complete search history.

(56) References Cited

U.S. PATENT DOCUMENTS

| | | | |
|---|---|---|---|
| 9,414,784 B1* | 8/2016 | Berme | ................ A61B 5/6823 |
| 2018/0192922 A1* | 7/2018 | Boucher | ............. A61B 5/1126 |

FOREIGN PATENT DOCUMENTS

| | | |
|---|---|---|
| JP | 2016112108 | 6/2016 |
| JP | 6319446 | 5/2018 |

* cited by examiner

*Primary Examiner* — Mohamed Charioui
*Assistant Examiner* — Christine Y Liao
(74) *Attorney, Agent, or Firm* — JCIPRNET

(57) ABSTRACT

An acceleration vector is detected in a kept-still state of a measurement target portion such as thighs of a target person to which an inertial sensor is attached, and further, another acceleration vector is detected in a state in which the target person is allowed to carry out exercise such that a posture of the measurement target portion is caused to change in a direction around a Yb axis with a Yb-axis direction of the measurement target portion maintained in a direction that perpendicularly intersects a vertical direction, direction in a sensor coordinate system the Yb-axis direction of the measurement target portion corresponds to is identified on the basis of a cross product vector of the acceleration vector and another acceleration vector.

7 Claims, 9 Drawing Sheets

METHOD FOR ESTIMATING ATTACHMENT POSTURE OF INERTIAL SENSOR

CROSS REFERENCE TO RELATED APPLICATION

This application claims the priority benefit of Japanese Patent Application No. 2019-043719, filed on Mar. 11, 2019. The entirety of the above-mentioned patent application is hereby incorporated by reference herein and made a part of this specification.

BACKGROUND

Technical Field

The disclosure relates to a method for estimating an attachment posture of an inertial sensor including an angular speed sensor with respect to a target person.

Description of Related Art

In the related art, technologies for observing exercise conditions of a target person by attaching an inertial sensor including an acceleration sensor and an angular speed sensor to a measurement target portion, such as the waist or a leg, of the target person and measuring an acceleration and an angular speed at the measurement target portion using the inertial sensor during exercise of the target person as can be seen in Patent Documents 1 and 2 are known (see Patent Documents 1 (Japanese Patent No. 6319446) and 2 (Japanese Patent Laid-Open No. 2016-112108), for example).

Patent Documents

Incidentally, it is necessary to identify a relative posture relationship between a measurement target portion and an inertial sensor attached thereto (an attachment posture of the inertial sensor with respect to the measurement target portion) in advance in order to observe which direction of the measurement target portion an acceleration has occurred in and which direction of the measurement target portion an angular speed has occurred in, on the basis of an acceleration and an angular speed detected by the inertial sensor attached to the measurement target portion.

Meanwhile, it is typically difficult to precisely attach the inertial sensor to the measurement target portion of the target person who is a human in a predetermined posture. In addition, it is desirable that a degree of freedom in attachment posture of the inertial sensor with respect to the measurement target portion be high in terms of easiness in attachment of the inertial sensor to the measurement target portion and the like.

Thus, there is a requirement for a method for appropriately estimating (identifying) a relative posture relationship between the measurement target portion and the inertial sensor attached thereto. Here, a method using geomagnetism is typically conceivable as the method. However, since geomagnetism is likely to be affected by an environment, it is difficult to highly reliably and stably estimate the relative posture relationship between the measurement target portion and the inertial sensor according to a method using geomagnetism.

Note that although Patent Documents 1 and 2 disclose technologies of performing calibration related to the posture of the inertial sensor, the technologies are not technologies for estimating the relative posture relationship between the measurement target portion and the inertial sensor.

SUMMARY

According to an embodiment of the disclosure, there is provided a method for estimating an attachment posture of an inertial sensor that is a method for estimating a relative posture relationship between a measurement target portion of a target person and the inertial sensor that is attached to the measurement target portion and includes an acceleration sensor capable of detecting accelerations in the respective coordinate axes in a sensor coordinate system, which is a three-dimensional coordinate system set in advance for the inertial sensor, the method including: a first process of detecting, with the acceleration sensor, a first acceleration vector that is an acceleration vector including a set of accelerations in three coordinate axis directions in the sensor coordinate system in a state in which the measurement target portion is kept still, and maintaining a first direction which is a predetermined direction set in advance with respect to the measurement target portion in a direction that perpendicularly intersects a vertical direction; a second process of allowing the target person to carry out exercise of causing a posture of the measurement target portion to change in a direction around an axis in the first direction with the first direction of the measurement target portion maintained in a direction that is the same as the direction in the first process; a third process of detecting, with the acceleration sensor, a second acceleration vector that is an acceleration vector including a set of accelerations in the three coordinate axis directions in the sensor coordinate system and has a direction that is different from a direction of the first acceleration vector, at one or more sampling times in the second process; and a fourth process of identifying first posture data that indicates which direction in the sensor coordinate system the first direction of the measurement target portion corresponds to, on the basis of one or more cross product vectors calculated in a cross product operation between each of one or more second acceleration vectors detected in the third process and the first acceleration vector detected in the first process (first aspect).

DESCRIPTION OF THE EMBODIMENTS

Figure 1:
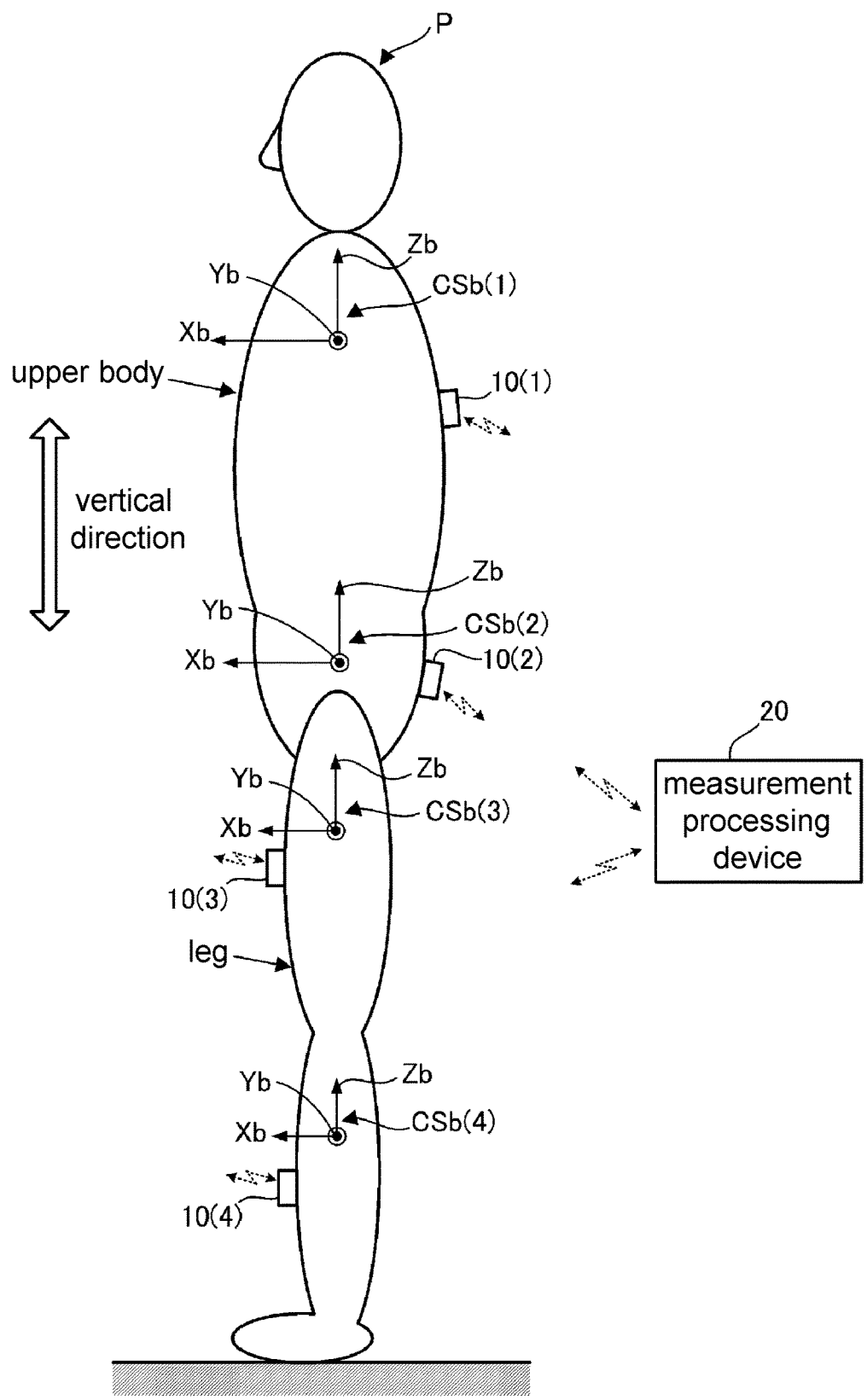
FIG. 1 is a configuration diagram of an entire system to which embodiments (a first embodiment and a second embodiment) of the disclosure are applied.

The disclosure was made in view of such background, and an object thereof is to provide a method by which it is possible to appropriately estimate a relative posture relationship between a measurement target portion of a target person and an inertial sensor attached thereto.

According to the disclosure, since the first acceleration vector is detected in the state in which the measurement target portion is kept still as described above in the first process, the second acceleration vector is detected in a state in which the exercise of the measurement target portion is being carried out, as described above in the second process, in the third process, the first acceleration vector and the second acceleration vector perpendicularly or substantially perpendicularly intersects the first direction.

Therefore, the cross product vector calculated through the cross product operation between each of the second acceleration vectors and the first acceleration vector is a vector in a direction that conforms to or substantially conforms to the first direction. Therefore, it is possible to identify the first posture data indicating which direction in the sensor coordinate system the first direction of the measurement target portion corresponds to, on the basis of one or more cross product vectors calculated in the third process, in the fourth process.

Therefore, according to the first aspect, it is possible to appropriately identify (estimate) the relative posture relationship regarding which direction the first direction of the measurement target portion of the target person corresponds to with respect to the inertial sensor.

In the first aspect, the exercise that the target person is allowed to carry out in the second process is preferably exercise of sequentially causing the posture of the measurement target portion to change in one of a forward direction and a reverse direction that is a direction around the axis in the first direction and causing the posture of the measurement target portion to change in the other direction, and the second acceleration vector detected in the third process preferably includes at least an acceleration vector at a timing of switching of a direction of a change in posture of the measurement target portion around the axis in the first direction (second aspect).

In this manner, it is possible to set the direction of the acceleration vector at the switching timing to be a direction that is relatively significantly different from the direction of the first acceleration vector. Thus, it is possible to calculate a highly reliable cross product vector as a vector in a direction that conforms to or substantially conforms to the first direction. Thus, it is possible to enhance reliability of the specification of the first direction based on the cross product vector.

In the first or second aspect, the measurement target portion is preferably lower legs or thighs of legs of the target person, and in a case in which the first direction is a left-right direction of the target person, the exercise that the target person is allowed to carry out in the second process is preferably exercise that includes at least bending and stretching the legs such that a posture of the thighs or the lower legs of the legs is caused to change in a pitch direction (third aspect).

In this manner, it is possible to easily and stably allow the target person to carry out the exercise of causing the posture of the thighs or the lower legs to change in the direction around the axis in the first direction with the first direction of the lower legs or the thighs of the target person kept constant in the second process. Therefore, it is possible appropriately detect the second acceleration vector in the direction that perpendicularly intersects the first direction in the third process. Thus, it is possible to highly reliably identify the first posture data related to the thighs or the lower legs of the legs of the target person.

Also, in the first or second aspect, the measurement target portion is preferably an upper body of the target person, and in a case in which the first direction is a left-right direction of the target person, the exerciser that the target person is allowed to carry out in the second process is preferably exercise that includes at least inclining the upper body of the target person in a pitch direction (fourth aspect).

In this manner, it is possible to easily and reliably allow the target person to carry out the exercise of causing the posture of the upper body to change in the direction around the axis in the first direction with the first direction of the upper body of the target person kept constant in the second process. Therefore, it is possible to appropriately detect the second acceleration vector in the direction that perpendicularly intersects the first direction in the third process. Thus, it is possible to highly reliably identify the first posture data related to the upper body of the target person.

The first to fourth aspects preferably further includes: a fifth process of allowing the target person to keep the measurement target portion still such that a second direction that is set in advance with respect to the measurement target portion as a direction that is different from the first direction is maintained in a vertical direction; a sixth process of detecting, with the acceleration sensor, a set of accelerations of the three coordinate axis directions in the sensor coordinate system at one or more sampling times in the fifth process; and a seventh process of identifying second posture data indicating which direction in the sensor coordinate system the second direction of the measurement target portion corresponds to, on the basis of one or more sets of accelerations detected in the fifth process (fifth aspect).

In this manner, the acceleration detected in the sixth process conforms to or substantially conforms to a gravity acceleration in the vertical direction, and the vertical direction is a direction in which the second direction of the measurement target portion is kept constant in the fifth process. Therefore, it is possible to identify the second posture data indicating which direction in the sensor coordinate system the second direction of the measurement target portion corresponds to in the seventh process, on the basis of one or more sets of accelerations detected in the sixth process.

Therefore, according to the fifth aspect, it is possible to appropriately identify (estimate) the relative posture relationship regarding which direction the second direction of the measurement target portion of the target person corresponds to with respect to the inertial sensor.

In the fifth aspect, the measurement target portion is preferably a lower leg or a thigh of a leg or an upper body of the target person, and the second direction is preferably a direction that is able to be directed in the vertical direction in a state in which the target person is standing up in an upright posture or in a state in which a body of the target person is kept still in contact with an object with a specific shape (sixth aspect).

In this manner, it is possible to easily realize the state of the target person in the fifth process.

In the fifth or sixth aspect, the method preferably further includes: an eighth process of identifying third posture data indicating which direction a third direction that perpendicularly intersects the first direction and the second direction corresponds to when seen in the sensor coordinate system on the basis of the first posture data identified in the fourth process and the second posture data identified in the seventh process, and in the eighth process, a vector obtained through a cross product operation of a vector in the first direction indicated by the first posture data and a vector in the second direction indicated by the second posture data is preferably identified as the third posture data (seventh aspect).

In this manner, it is possible to easily identify the third posture data indicating which direction the third direction that perpendicularly intersects the first direction and the second direction of the measurement target portion corresponds to when seen in the sensor coordinate system through the cross product operation of the vector in the first direction indicated by the first posture data that has already been identified and the vector in the second direction indicated by the second posture data that has already been identified.

In addition, a special posture relationship between the measurement target portion and the inertial sensor is identified by identifying the first posture data, the second posture data, and the third posture data that represent the three directions, namely the first direction, the second direction, and the third direction of the measurement target portion, and for example, it is possible to transform an arbitrary vector when seen in the sensor coordinate system into a vector when seen in a three-dimensional coordinate system set for a measurement target portion.

First Embodiment

A first embodiment of the disclosure will be described below with reference to FIGS. 1 to 6. Referring to FIG. 1, inertial sensors 10(i) (i=1, 2, ... ) are attached to a plurality of measurement target portions of a target person P (illustration of arms is omitted) in the embodiment. For example, an upper portion of an upper body and a waist portion (a lower portion of the upper body) and thighs and lower legs of the respective legs of the target person P may be defined as measurement target portions, and the respective inertial sensors 10(1), 10(2), 10(3), and 10(4) may be attached to the respective measurement target portions via appropriate attachment members such as belts, which are not illustrated, such that the inertial sensors moves integrally with the measurement target portions.

Note that the respective inertial sensors 10(1), 10(2), 10(3), and 10(4) may be provided in a tool attached to the target person P, such as a walking assist device, for example. In the following description, the inertial sensors 10(1), 10(2), 10(3), and 10(4) will simply be referred to as inertial sensors 10 when it is not necessary to distinguish each of the inertial sensors.

Figure 2:
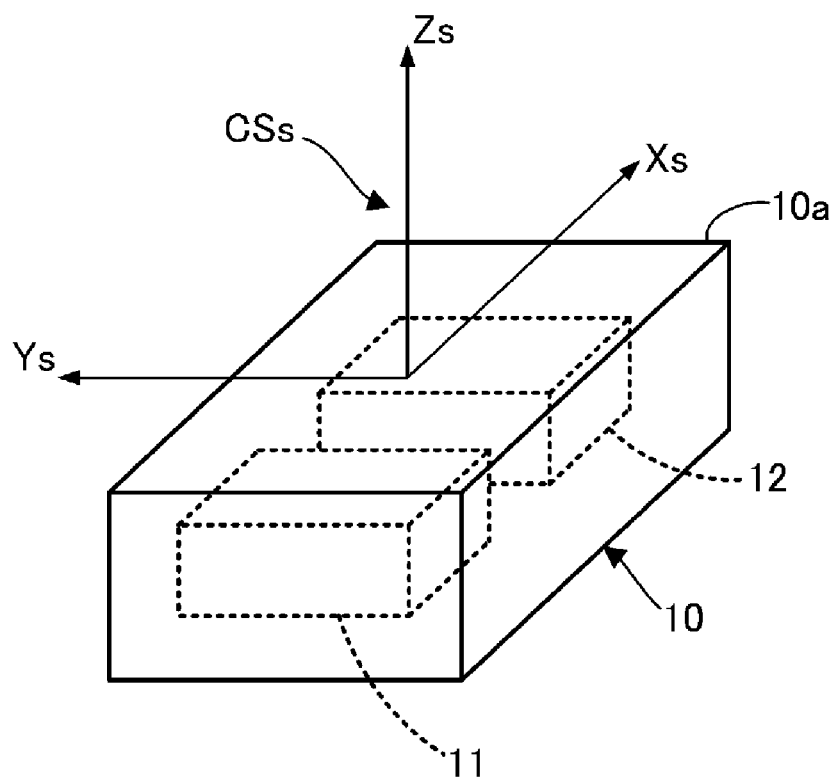
FIG. 2 is a perspective view illustrating an inertial sensor and a sensor coordinate system included in the system in FIG. 1.

Each inertial sensor 10 includes an angular speed sensor 11 and an acceleration sensor 12 in a case body 10a as illustrated in FIG. 2. The angular speed sensor 11 is a sensor with a known configuration capable of detecting angular speeds generated in the inertial sensor 10 in directions of the respective coordinate axes Xs, Ys, and Zs (directions around the respective coordinate axes Xs, Ys, and Zs) in the sensor coordinate system CSs that is a three-dimensional coordinate system (three-axis orthogonal coordinate system) set (defined) in advance for each inertial sensor 10. Also, the acceleration sensor 12 is a sensor with a known configuration capable of detecting parallel acceleration generated in the inertial sensor 10 in the directions of the respective coordinate axes Xs, Ys, and Zs (hereinafter, also referred to as an Xs axis, a Ys axis, and a Zs axis, respectively) in the sensor coordinate system CSs.

Note that orientations of the respective coordinate axes Xs, Ys, and Zs in the sensor coordinate system CSs illustrated in FIG. 2 are illustrative orientations, and the orientations of the respective coordinate axes Xs, Ys, and Zs in the sensor coordinate system CSs in each inertial sensor 10 can arbitrarily be set in terms of design. For example, the Zs-axis direction and the Xs-axis direction or the Ys-axis direction in the illustrated example may be exchanged.

In addition, a wireless communication machine, which is not illustrated, is mounted in each inertial sensor 10, and the inertial sensor 10 can perform wireless communication with an external measurement processing device 20. The measurement processing device 20 can be configured of, for example, a personal computer, a smartphone, a tablet terminal, or a dedicated measurement gauge. In addition, the measurement processing device 20 can successively acquire detection data obtained by the angular speed sensor 11 and the acceleration sensor 12 from each inertial sensor 10 through communication with each inertial sensor 10.

Note that the communication between each inertial sensor 10 and the measurement processing device 20 may be performed via a relay machine attached to the target person P, for example. In this case, the communication between each inertial sensor 10 and the relay machine may be wired communication. Further, the measurement processing device 20 may be able to be attached to the target person P, or the measurement processing device 20 may be a device provided in a device to be attached to the target person P, such as a walking assist device. In these cases, the communication between each inertial sensor 10 and the measurement processing device 20 may be wired communication.

A body-side coordinate system CSb(i) (i=1, 2, ... ) that is a three-dimensional coordinate system (three-axis orthogonal coordinate system) is set (defined) in advance as illustrated as an example in FIG. 1, for example, for each measurement target portion of the target person P.

Specifically, a body-side coordinate system CSb(1) in which a front-back direction of an upper portion of the upper body, a left-right direction of the upper portion of the upper body, and a body core axis direction of the upper portion of the upper body are defined as the directions of the three respective coordinate axes Xb, Yb, and Zb is set for the upper portion of the upper body of the target person P to which the inertial sensor 10(1) is attached.

Also, a body-side coordinate system CSb(2) in which a front-back direction of a waist portion, a left-right direction of the waist portion, and a body core axis direction of the waist portion, for example, are defined as the respective directions of the three coordinate axes Xb, Yb, and Zb is set for the waist portion (a lower portion of the upper body) to which the inertial sensor 10(2) is attached.

In addition, a body-side coordinate system CSb(3) in which a front-back direction of a thigh, a left-right direction of the thigh, and a longitudinal direction of the thigh are defined as the respective directions of the three coordinate axes Xb, Yb, and Zb is set for the thigh of each leg to which the inertial sensor 10(3) is attached.

Also, a body-side coordinate system CSb(4) in which a front-back direction of a lower leg, a left-right direction of the lower leg, and a longitudinal direction of the lower leg are defined as the respective directions of the three coordinate axes Xb, Yb, and Zb, for example, is set for the lower leg of each leg to which the inertial sensor 10(4) is attached.

Therefore, the body-side coordinate systems CSb(I) (i=1, 2, ... ) at each measurement target portion is set such that the three coordinate axes Xb, Yb, and Zb (hereinafter, also referred to as an Xb axis, a Yb axis, and a Zb axis) in each body-side coordinate system CSb(i) conforms to or substantially conforms to the front-back direction, the left-right direction, and the vertical direction (gravity direction) of the target person P, respectively, in a posture state of each measurement target portion in a state in which the target person P is standing up in an upright posture on a horizontal floor surface (the state illustrated in FIG. 1) in the embodiment.

Therefore, the body-side coordinate systems CSb(1), CSb(2), CSb(3), and CSb(4) will simply be referred to as body-side coordinate systems CSb when it is not necessary to distinguish each of the body-side coordinate systems in the following description. Note that orientations of the respective coordinate axes Xb, Yb, and Zb in each body-side coordinate system CSb can arbitrarily be set in terms of design. For example, the Zb-axis direction and the Xb-axis direction or the Yb-axis direction in each body-side coordinate system CSb may be replaced from those in the aforementioned example.

In the system that includes the inertial sensors 10(i) (i=1, 2, ... ) and the measurement processing device 20 as described above, the measurement processing device 20 can observe exercise conditions of the upper body of the respective legs of the target person P using detection data such as angular speeds and accelerations obtained by the respective inertial sensors 10. For example, it is possible to observe a direction and a degree of acceleration of each measurement target portion that has occurred, how the direction and the degree of the acceleration change with time, a direction in which the posture of each measurement target portion changes and a degree of angular speed with which the posture of each measurement target portion changes, how the direction and the degree of the angular speed change with time, or the like during exercise, such as walking, of the target person P.

Further, it is also possible to successively estimate a posture of each measurement target portion when seen in a global coordinate system (a world coordinate system set in an exercise environment of the target person P) through an arithmetic operation of a strapdown scheme from the detection data such as the angular speed and the acceleration obtained by each inertial sensor 10, for example.

In this case, since the detection data obtained from each inertial sensor 10 is detection data of the angular speed or the acceleration when seen in the sensor coordinate system CSs of each inertial sensor 10, it is necessary to identify a relative posture relationship between the body-side coordinate system CSb at each measurement target portion and the sensor coordinate system CSs of the inertial sensor 10 attached to the measurement target portion (in other words, a relative posture relationship between each measurement target portion and the inertial sensor 10 attached thereto) for observing the exercise conditions of the target person P as described above.

On the other hand, when each inertial sensor 10 is attached to the measurement target portion of the target person P, it is typically difficult to precisely attach the inertial sensor 10 to the measurement target portion such that the relative posture relationship between the body-side coordinate system CSb of the measurement target portion and the sensor coordinate system CSs of the inertial sensor 10 (the relative posture relationship between each measurement target portion and the inertial sensor 10) conforms to a desired posture relationship.

Thus, processing of identifying (estimating) the relative posture relationship between the body-side coordinate system CSb of each measurement target portion and the sensor coordinate system CSs of the inertial sensor 10 attached to the measurement target portion in advance is executed before the observation of the exercise conditions of the target person P in the embodiment.

Specifically, processing of estimating which orientation the orientation of each of the coordinate axes Xb, Yb, and Zb in the body-side coordinate system CSb at each measurement target portion corresponds to when seen in the sensor coordinate system CSs of the inertial sensor 10 attached to the measurement target portion (hereinafter, referred to as coordinate axis direction estimation processing) is performed.

In this case, the coordinate axis direction estimation processing for the coordinate axis Zb among the three coordinate axes Xb, Yb, and Zb in each body-side coordinate system CSb is performed as follows. In other words, the target person P stands up and is kept still in the upright posture as illustrated in FIG. 1 in the coordinate axis direction estimation processing. Note that at this time, the standing state of the target person P may be assisted by an arbitrary toop or a helper such that a minimum force in the transverse direction acts on the target person P.

Figure 3:
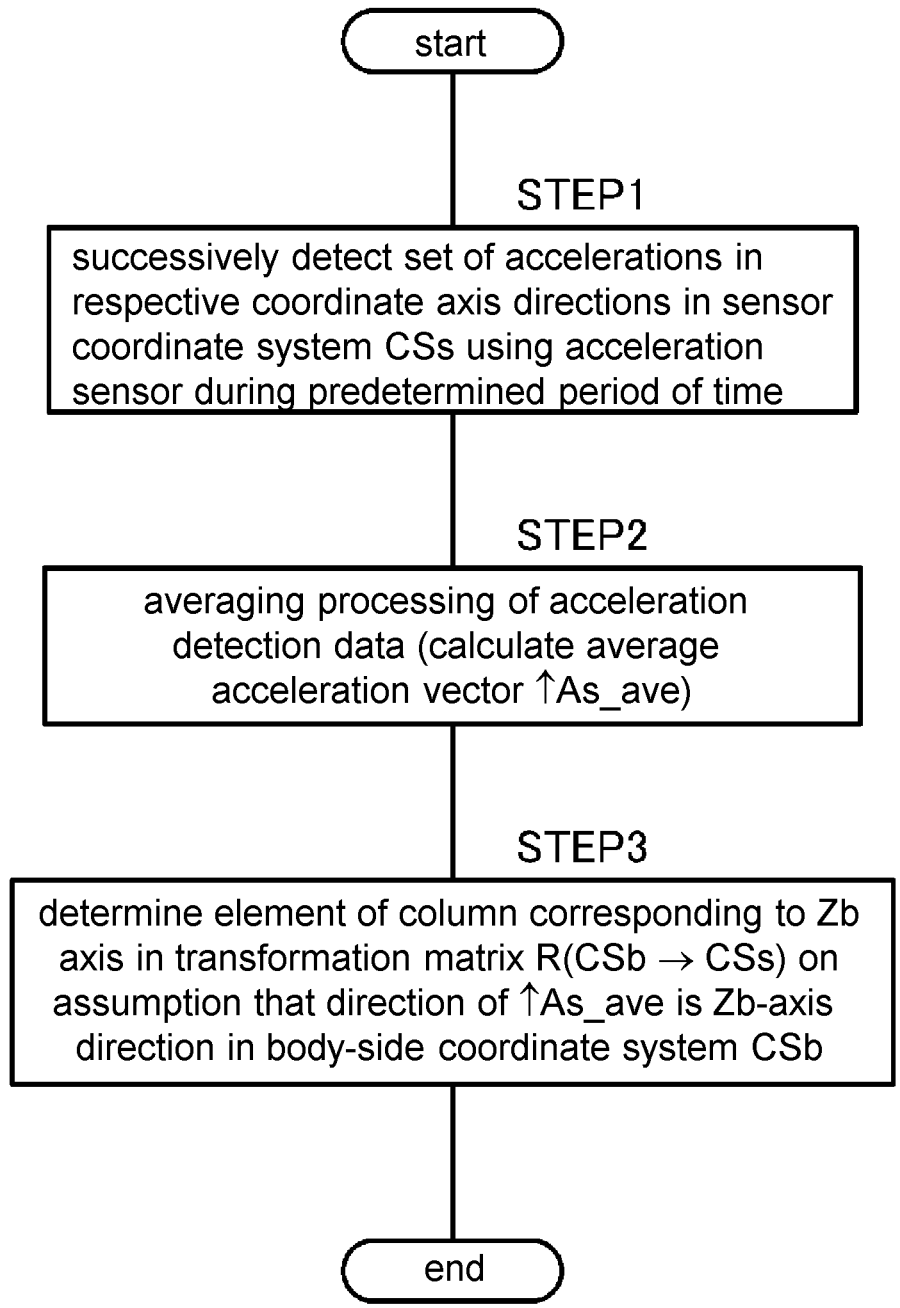
FIG. 3 is a flowchart illustrating processing for estimating a direction of a coordinate axis Zb of a body-side coordinate system CSb at a measurement target portion of a target person according to the first embodiment.

In the state in which the target person P is standing up and kept still in the upright posture in this manner, the measurement processing device 20 executes the processing illustrated in FIG. 3 for each measurement target portion. Specifically, in STEP 1, the measurement processing device 20 detects a set of accelerations in the respective coordinate axis direction in the sensor coordinate system CSs of the inertial sensor 10 (in other words, a set of elements in the directions of the respective coordinate axes Xs, Ys, and Zs of acceleration vectors that have been generated in the inertial sensor 10) at a predetermined sampling cycle using the acceleration sensor 12 of the inertial sensor 10 at each measurement target portion during a predetermined period of time.

In this manner, the measurement processing device 20 acquires detection data of the acceleration vectors (acceleration vectors when seen in the sensor coordinate system CSs of the inertial sensor 10) of the inertial sensor 10 at a plurality of sampling times for each measurement target portion in the state in which the target person P is standing up and kept still in the upright posture.

Next, in STEP 2, the measurement processing device 20 executes processing of averaging a plurality of pieces of detection data of the acceleration vectors when seen in the sensor coordinate system CSs of the inertial sensor 10 for each measurement target portion. In other words, the measurement processing device 20 calculates an average acceleration vector ↑As_ave that is a set of acceleration average values in the directions of the respective coordinate axes Xs, Ys, an Zs by calculating an average value of the detection values of accelerations in the directions of the respective coordinate axes Xs, Ys, and Zs in the sensor coordinate system CSs of the inertial sensor 10 at each measurement target portion. Note that the reference signs to which "↑" is applied represent vectors in the specification.

Here, the acceleration vector detected in STEP 1 is an acceleration vector detected by the acceleration sensor 12 of each inertial sensor 10 in a state in which the target person P is standing up and kept still in the upright posture, and the acceleration vector conforms to or substantially conforms to a gravity acceleration vector in the vertical direction. In addition, the direction (Zb-axis direction) of the coordinate axis Zb among the respective coordinate axes Xb, Yb, and Zb in the body-side coordinate system CSb at each measurement target portion conforms to or substantially conforms to the vertical direction in the state in which the target person is standing up and kept still in the upright posture in the embodiment.

Therefore, it is possible to regard the direction of the average acceleration vector ↑As_ave calculated in STEP 2 for each measurement target portion as representing the Zb-axis direction of the body-side coordinate system CSb at each measurement target portion when seen in the sensor coordinate system CSs of the inertial sensor 10 at the measurement target portion.

Thus, the measurement processing device 20 then identifies (estimates) an element of a column corresponding to the Zb axis of a transformation matrix R (CSb→CSs) for performing coordinate transformation of the vector amount from the body-side coordinate system CSb to the sensor coordinate system CSs of the inertial sensor 10 at each measurement target portion on the assumption that the direction of the average acceleration vector ↑As_ave calculated in STEP 2 is the Zb-axis direction in the body-side coordinate system CSb at the measurement target portion in STEP 3.

The aforementioned transformation matrix R (CSb→CSs) is a three-dimensional matrix that transforms coordinates from an arbitrary vector ($\alpha xb$, $\alpha yb$, $\alpha zb$) seen in the body-side coordinate system CSb to a vector ($\alpha xs$, $\alpha ys$, $\alpha zs$) seen in the sensor coordinate system CSs as represented by Equation (1) below. Note that each of $\alpha xb$, $\alpha yb$, and $\alpha zb$ represents a value in each of the directions of the coordinate axes Xb, Yb, and Zb in the body-side coordinate system CSb, each of $\alpha xs$, $\alpha ys$, and $\alpha zs$ represents a value in each of the directions of the coordinate axes Xs, Ys, and Zs in the sensor coordinate system CSs, and the suffix "T" means transposition. Note that each of vectors $(e11, e21, e31)^T$, $(e12, e22, e32)^T$, and $(e13, e23, e33)^T$ of the respective columns in the transformation matrix R (CSb→CSs) is a unit vector. Also, a transposed matrix R $(CSb→CSs)^T$ of the transformation matrix R (CSb→CSs) is a transformation matrix R (CSs→CSb) (=an inverse matrix of R(CSb→CSs)) in order to transform coordinates from the sensor coordinate system CSs to the body-side coordinate system CSb.

[Mathematical formula 1]

$$\begin{pmatrix} \alpha xs \\ \alpha ys \\ \alpha zs \end{pmatrix} = R(CSb \to CSs) \cdot \begin{pmatrix} \alpha xb \\ \alpha yb \\ \alpha zb \end{pmatrix} \quad (1)$$

$$= \begin{pmatrix} e11 & e12 & e13 \\ e21 & e22 & e23 \\ e31 & e32 & e33 \end{pmatrix} \cdot \begin{pmatrix} \alpha xb \\ \alpha yb \\ \alpha zb \end{pmatrix}$$

In this case, the column corresponding to the Zb axis of the transformation matrix R (CSb→CSs) is the right side of Equation (1) in the transformation matrix R(CSb→CSs) and is a column applied to the third element $\alpha zb$ (the element in the Zb-axis direction) of the vector $(\alpha xb, \alpha yb, \alpha zb)^T$, that is, the third column. Also, in a case in which the direction of the average acceleration vector ↑As_ave calculated in STEP 2 for each measurement target portion is regarded as the Zb-axis direction in the body-side coordinate system CSb at each measurement target portion, the average acceleration vector ↑As_ave is a vector that is proportional to $(e13, e23, e33)^T$ that is a vector calculated by assigning $(0, 0, 1)^T$ to $(\alpha xb, \alpha yb, \alpha zb)^T$ in the right side of Equation (1).

Thus, in STEP 3, the measurement processing device 20 calculates the vector $(e13, e23, e33)^T$ of the third column in the transformation matrix R(CSb→CSs) for each measurement target portion using Equation (2a) or (2b) below. In other words, the measurement processing device 20 calculates the vector $(e13, e23, e33)^T$ of the third column in the transformation matrix R(CSb→CSs) by transforming the average acceleration vector ↑As_ave into a unit vector.

Note that which of Equations (2a) and (2b) is to be used to calculate the vector $(e13, e23, e33)^T$ of the third column depends on to which direction of each coordinate axis the positive direction of each coordinate axis in each of the sensor coordinate system CSs and the body-side coordinate system CSb is to be set.

[Mathematical formula 2]

$$\begin{pmatrix} e13 \\ e23 \\ e33 \end{pmatrix} = \uparrow As\_ave / |\uparrow As\_ave| \quad (2a)$$

or $$\begin{pmatrix} e13 \\ e23 \\ e33 \end{pmatrix} = -\uparrow As\_ave / |\uparrow As\_ave| \quad (2b)$$

In this manner, the element of the column corresponding to the Zb axis of the transformation matrix R(CSb→CSs) is estimated (identified) for each measurement target portion. In the embodiment, the coordinate axis direction estimation processing for the coordinate axis Zb of each body-side coordinate system CSb is performed as described above.

Note that in the embodiment, the Zb-axis direction in the body-side coordinate system CSb at each measurement target portion corresponds to the second direction in the disclosure, and the vector $(e13, e23, e33)^T$ of the third column of the transformation matrix R(CSb→CSs) corresponds to the second posture data in the disclosure.

Figure 4:
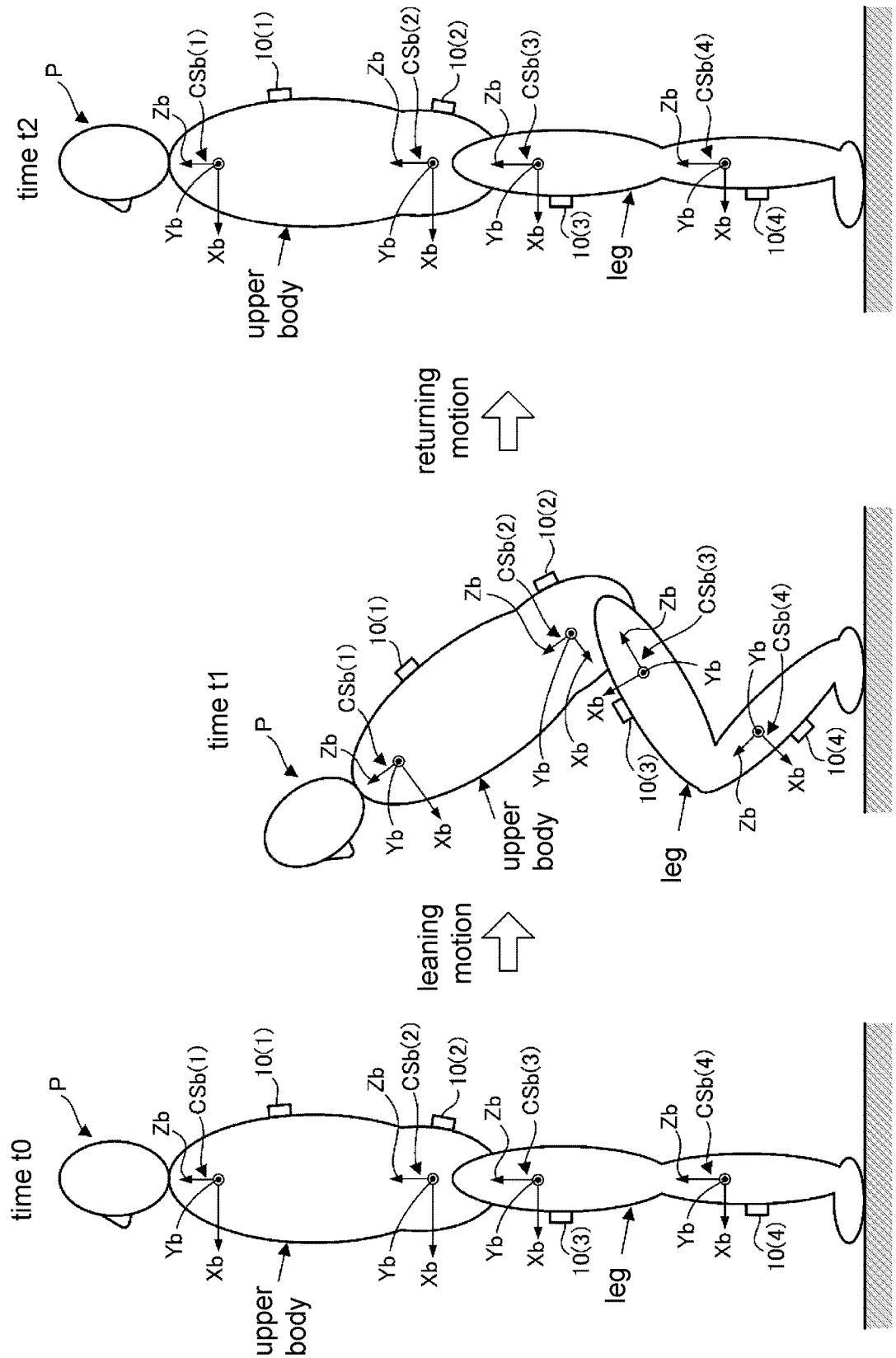
FIG. 4 is a diagram illustrating an operation executed by the target person for processing for estimating a direction of a coordinate axis Yb in the body-side coordinate system CSb at the measurement target portion of the target person according to the first embodiment.

Next, the coordinate axis direction estimation processing for the coordinate axis Yb, for example, among the three coordinate axes Xb, Yb, and Zb in each body-side coordinate system CSb is performed as follows. In other words, the target person P is kept still in a state (the state at the time t0) in which the target person P is standing up such that the Yb-axis direction (the left-right direction of the target person P) in the body-side coordinate system CSb at each measurement target portion corresponds to the direction (horizontal direction) that perpendicularly intersects the vertical direction as illustrated in FIG. 4 first in the coordinate axis direction estimation processing. The kept-still state is a state before the target person P carries out a leaning motion and a returning motion, which will be described later. Note that a posture state of the target person P in the kept-still state is not necessarily a state in which the target person is standing up in the upright posture. For example, the upper body of the target person P may be inclined forward to some extent, or the respective legs may be bent in the pitch direction (the direction around the axis in the left-right direction of the target person P) to some extent.

Figure 5:
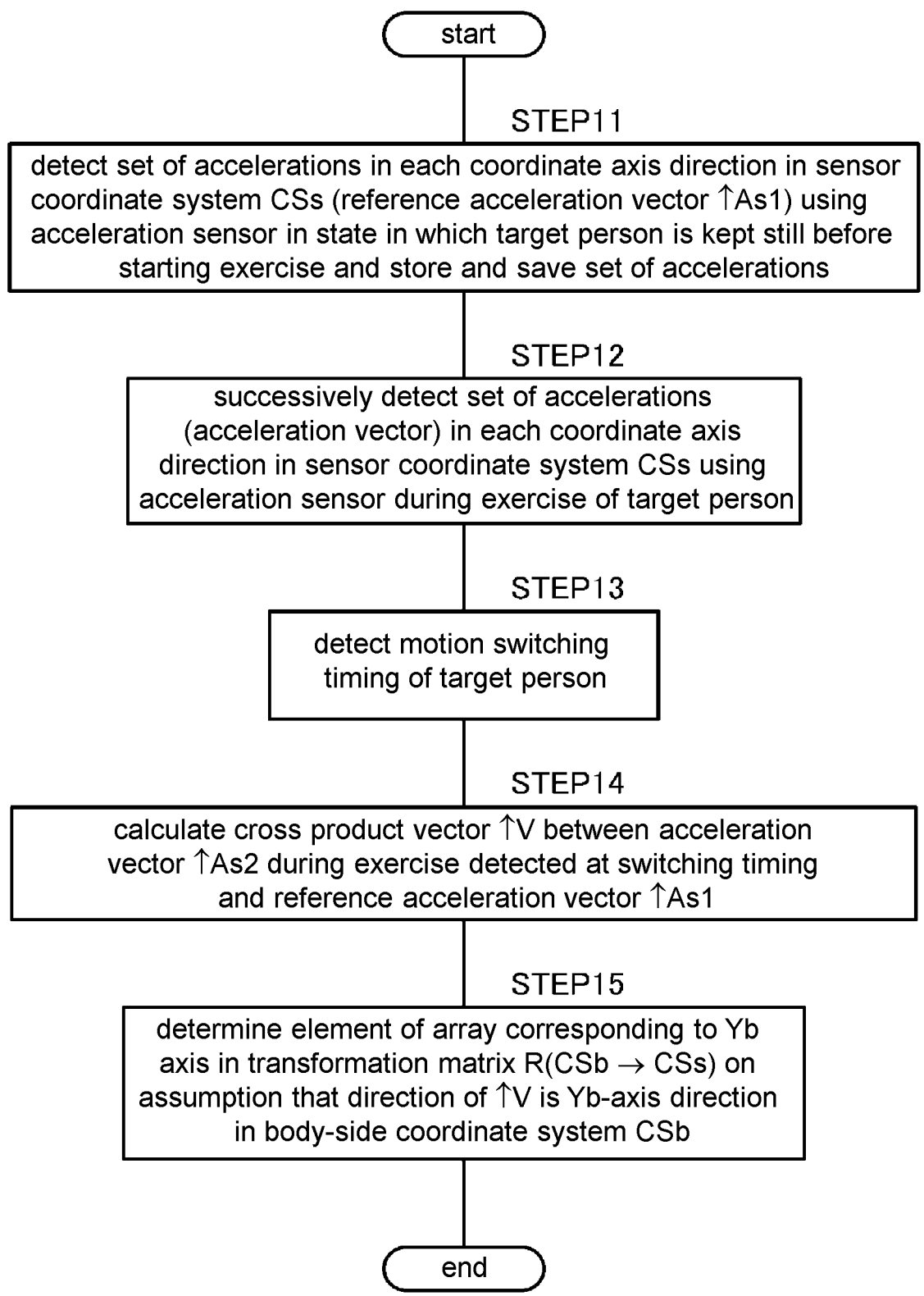
FIG. 5 is a flowchart illustrating processing for estimating the direction of the coordinate axis Yb in the body-side coordinate system CSb at the measurement target portion of the target person according to the first embodiment.
Figure 6:
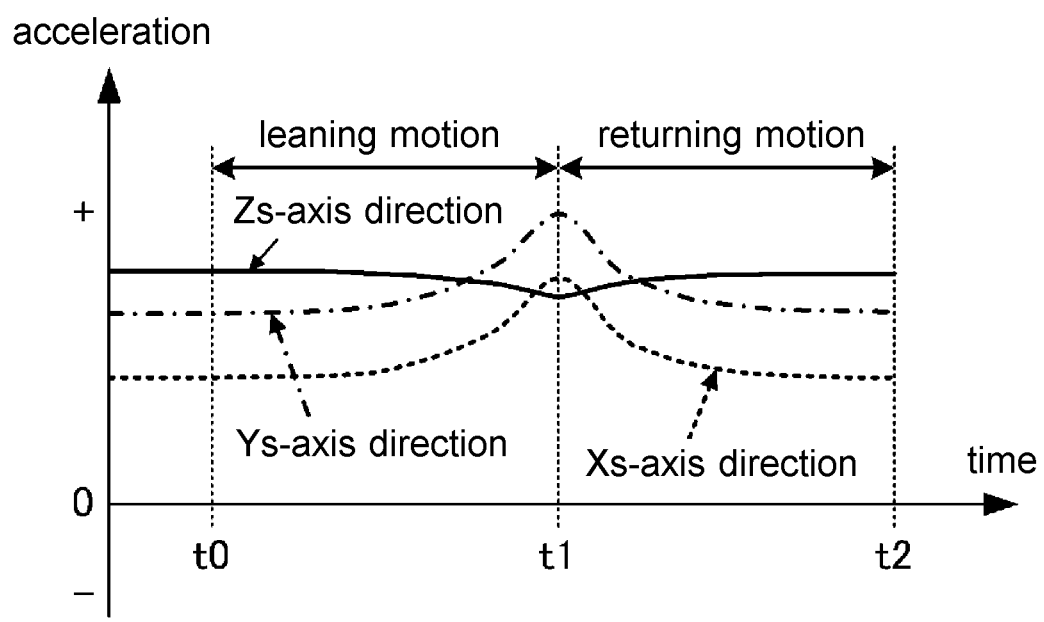
FIG. 6 is a graph illustrating, as an example, a change in acceleration with time that is detected in processing in STEP 12 in the flowchart in FIG. 5.

The measurement processing device 20 executes the processing in STEP 11 in the flowchart in FIG. 5 in the state in which the target person P is standing up and kept still as described above. In STEP 11, the measurement processing device 20 detects a set of accelerations in each coordinate axis direction in the sensor coordinate system CSs of the inertial sensor 10 (in other words, a set of elements in the directions of the respective coordinate axes Xs, Ys, and Zs of the acceleration vector that has occurred in the inertial sensor 10) using the acceleration sensor 12 in the inertial sensor 10 at each measurement target portion and stores and saves the detected acceleration vector as a reference acceleration vector ↑As1. The reference acceleration vector ↑As1 corresponds to the acceleration vector caused by a gravity acting on the inertial sensor 10 and is a vector that conforms to or substantially conforms to the vertical direction (gravity direction). Also, the reference acceleration vector ↑As1 corresponds to the first acceleration vector according to the disclosure.

Note that an average acceleration vector ↑As_ave obtained through the processing in STEPS 1 and 2 in FIG. 3 described above, for example, in the state in which the target person P is standing up and kept still may be set as the reference acceleration vector ↑As1.

Next, the target person P performs a leaning motion in which the upper body is inclined forward in the pitch direction from the kept-still state in STEP 11 (the state at the time t0) and both legs are bent in the pitch direction (more specifically, both legs are bent such that the postures of thighs and lower legs of the respective legs are caused to change in the pitch direction) as illustrated in FIG. 4, for example, then the target person P executes a returning motion of returning to the state in which the target person P is standing up in the upright posture (the state at the time t2) by causing the postures of the upper body and the thighs and the lower legs of the respective legs to change in the directions opposite to the directions of the leaning motion from the state in which the target person P leans through the leaning motion (the state at the time t1). Note that in this case, an appropriate tool, a helper, or the like may assist the aforementioned leaning motion and the returning motion of the target person P. Also, these motions of the target person P may be carried out slowly.

The measurement processing device 20 executes processing in and after STEP 12 in the flowchart in FIG. 5 for each measurement target portion in parallel to the exercise of the target person P in this manner. Specifically, in STEP 12, the measurement processing device 20 successively detects a set of accelerations in each coordinate axis direction in the sensor coordinate system CSs of the inertial sensor 10 (in other words, a set of elements in the directions of the respective coordinate axes Xs, Ys, Zs of the acceleration vector that has occurred in the inertial sensor 10) using the acceleration sensor 12 in the inertial sensor 10 at each measurement target portion during the exercise of the target person P in a predetermined sampling cycle.

In this manner, the measurement processing device 20 successively acquires detection data of the acceleration vector of the inertial sensor 10 (the acceleration vector when seen in the sensor coordinate system CSs of the inertial sensor 10) for each measurement target portion during the exercise of the target person P sequentially carrying out the leaning motion and the returning motion. In this case, the detection values of the elements in the directions of the respective coordinate axes Xs, Ys, and Zs of the acceleration vector change with time with a waveform pattern as illustrated as an example by the graph in FIG. 6, for example, in a case in which the leaning motion and the returning motion are performed slowly.

The measurement processing device 20 successively acquires the detection data of the acceleration vector in this manner and executes detection of a switching timing of the motion of the target person P (a timing at which the leaning motion shifts to the returning motion) on the basis of a time sequence of the detection data of the acceleration vector for each measurement target portion in STEP 13. The switching timing is a timing at which the direction of a change in posture at each measurement target portion (a forward direction and a reverse direction in the pitch direction) is switched in other words.

In STEP 13, the measurement processing device 20 identifies a timing at which a detection value of an element in any of the coordinate axis directions among detection data of elements in the respective coordinate axis directions of the acceleration on which low pass type filtering processing has been performed shifts from an increase to a decrease or from a decrease to an increase (a timing at which the detection value becomes a peak value), for each measurement target portion, for example, and detects the timing as a motion switching timing of the target person P.

Note that the switching timing may be detected on the basis of a waveform (a waveform of temporal change in elements in the respective coordinate axis directions) represented by a time sequence of the detection data of the elements in the respective coordinate axis directions of the acceleration vector after the target person P ends the leaning motion and the returning motion, for example. Alternatively, the switching timing may be detected on the basis of change in orientation of an angular speed vector detected by the angular speed sensor 11 of the inertial sensor 10.

Next, in STEP 14, the measurement processing device 20 calculates a cross product vector ↑V that perpendicularly intersects the acceleration vector ↑As2 during the exercise, which is an acceleration vector detected at the switching timing, and the reference acceleration vector ↑As1 detected in STEP 11 described above through the cross product operation therebetween for each measurement target portion. Note that the acceleration vector ↑As2 during the exercise corresponds to the second acceleration vector according to the disclosure.

Here, since the acceleration vector detected in STEP 12 is an acceleration vector detected by the acceleration sensor 12 in each inertial sensor 10 in an exercise state in which the target person P is sequentially performing the leaning motion and the returning motion from the state in which the target person P is standing up in STEP 11, the direction of the acceleration vector is maintained in a state in which the direction perpendicularly or substantially perpendicularly intersects the left-right direction of the target person P when the target person P is carrying out each of the leaning motion and the returning motion. Therefore, both the acceleration vector ↑As2 during the exercise detected at the switching timing for each measurement target portion and the reference acceleration vector ↑As1 are vectors that perpendicularly or substantially perpendicularly intersect the direction of the Yb axis, which is a coordinate axis in the left-right direction of the target person P in the body-side coordinate system CSb at each measurement target portion.

In addition, since the acceleration vector ↑As2 during the exercise detected at the switching timing is a composite acceleration of the gravity acceleration and the exercise acceleration that accompanies the exercise of the target person P, the direction of the acceleration vector ↑As2 during the exercise is a direction that is different from the direction (substantially vertical direction) of the reference acceleration vector ↑As1.

Therefore, the direction of the cross product vector ↑V calculated through the cross product operation between the acceleration vector ↑As2 during the exercise at the switching timing and the reference acceleration vector ↑As1 for each measurement target portion conforms to or substantially conforms to the Yb-axis direction in the body-side coordinate system CSb at each measurement target portion.

Therefore, the direction of the cross product vector ↑V calculated in STEP 14 for each measurement target portion can be regarded as representing the Yb-axis direction in the body-side coordinate system CSb at each measurement target portion when seen in the sensor coordinate system CSs of the inertial sensor 10 at the measurement target portion.

Thus, the measurement processing device 20 determines an element of the column corresponding to the Yb axis in the transformation matrix R(CSb→CSs) on the assumption that the direction of the cross product vector ↑V calculated in STEP 14 corresponds to the Yb-axis direction in the body-side coordinate system CSb at each measurement target portion for each measurement target portion in next STEP 15.

In this case, the column corresponding to the Yb axis of the transformation matrix R (CSb→CSs) is a column applied to the second element αyb (the element in the Yb-axis direction) of the vector (αxb, αyb, αzb)$^T$ in the right side of Equation (1) in the transformation matrix R (CSb→CSs), that is, a second column. In addition, in a case in which the direction of the cross product vector ↑V calculated in STEP 14 for each measurement target portion is regarded as the Yb-axis direction in the body-side coordinate system CSb at the measurement target portion, the cross product vector ↑V is a vector that is proportional to (e21, e22, e23)$^T$ that is a vector calculated by assigning (0, 1, 0)$^T$ to (αxb, αyb, αzb)$^T$ in the right side of Equation (1) described above.

Thus, in STEP 13, the measurement processing device 20 calculates the vector (e12, e22, e32)$^T$ of the second column in the transformation matrix R (CSb→CSs) for each measurement target portion by Equation (3a) or (3b) below. In other words, the measurement processing device 20 calculates the vector (e12, e22, e32)$^T$ of the second column in the transformation matrix R (CSb→CSs) by transforming the cross product vector ↑V for each measurement target portion into a unit vector.

Note that which of Equations (3a) and (3b) is used to calculate the vector (e12, e22, e32)$^T$ of the second column depends on to which orientation of the direction of each coordinate axis the positive direction of each coordinate axis in each of the sensor coordinate system CSs and the body-side coordinate system CSb is set.

[Mathematical formula 3]

$$\begin{pmatrix} e12 \\ e22 \\ e32 \end{pmatrix} = \uparrow V / |\uparrow V| \tag{3a}$$

or $$\begin{pmatrix} e12 \\ e22 \\ e32 \end{pmatrix} = -\uparrow V / |\uparrow V| \tag{3b}$$

In this manner, the element of the column corresponding to the Yb-axis element in the transformation matrix R(CSb→CSs) is estimated (identified) for each measurement target portion. Note that the cross product vector ↑V calculated in STEP 14 may be a unit vector, and in this case, the cross product vector ↑V may be identified directly as the vector (e12, e22, e32)$^T$ of the second column. In the embodiment, the coordinate axis direction estimation processing for the coordinate axis Yb in each body-side coordinate system CSb is performed as described above.

Note that in the embodiment, the Yb-axis direction in the body-side coordinate system CSb at each measurement target portion corresponds to the first direction according to the disclosure, and the vector (e12, e22, e32)$^T$ of the second column in the transformation matrix R (CSb→CSs) corresponds to the first posture data according to the disclosure.

Next, coordinate axis direction estimation processing for the remaining coordinate axis Xb among the three coordinate axes Xb, Yb, and Zb in each body-side coordinate system CSb is performed as follows. In other words, the measurement processing device 20 obtains a vector (e11, e21, e31)$^T$ of the first column corresponding to an Xb-axis element in the transformation matrix R(CSb→CSs) as a unit vector that perpendicularly intersects the vector (e12, e22, e32)$^T$ of the second column and the vector (e13, e23, e33)$^T$ of the third column obtained as described above in the coordinate axis direction estimation processing. Specifically, the vector (e11, e21, e31)$^T$ of the first column is calculated through a cross product operation (an arithmetic operation of a vector product) of the vector (e12, e22, e32)$^T$ of the second column and the vector (e13, e23, e33)$^T$ of the third column in this case.

Note that in the embodiment, the Xb-axis direction in the body-side coordinate system CSb at each measurement target portion corresponds to the third direction according to the disclosure, and the vector (e11, e21, e31)$^T$ of the first column in the transformation matrix R(CSb→CSs) corresponds to the third posture data according to the disclosure.

In the embodiment, the element of each column in the transformation matrix R(CSb→CSs) is obtained for each measurement target portion as described above. In this manner, the relative posture relationship between the sensor coordinate system CSs and the body-side coordinate system CSb (in other words, the relative posture relationship between the inertial sensor 10 and the measurement target portion) is identified by the transformation matrix R(CSb→CSs) for each measurement target portion.

In this case, the coordinate axis direction estimation processing related to the coordinate axis Zb in the body-side coordinate system CSb at each measurement target portion is performed using the detection data of the accelerations in the state in which the target person P is standing up in the upright posture. In addition, it is possible to relatively stably maintain the Zb-axis direction that is a direction of one of the coordinate axes in the body-side coordinate system CSb at each measurement target portion in a state in which the Zb-axis direction conforms to or substantially conforms to the vertical direction in the state in which the target person P is standing up in the upright posture. Therefore, it is possible to identify the column vector (the vector of the third column) in the transformation matrix R(CSb→CSs) representing the Zb-axis direction in the body-side coordinate system CSb when seen in the sensor coordinate system CSs for each measurement target portion with high reliability.

Also, the coordinate axis direction estimation processing related to the coordinate axis Yb in the body-side coordinate system CSb when seen in the sensor coordinate system CSs at each measurement target portion is performed using the reference acceleration vector ↑As1 detected in the state in which the target person P is standing up and kept still and the acceleration vector ↑As2 during the exercise detected at one timing (the switching timing in the embodiment) in the state in which the target person P is sequentially carrying out the leaning motion and the returning motion.

In this case, the reference acceleration vector ↑As1 detected in the state in which the target person P is standing up and kept still precisely becomes a vector in the vertical direction (a vector that perpendicularly intersects the left-right direction of the target person P). Also, it is possible to relatively stably maintain the Yb-axis direction in the body-side coordinate system CSb at each measurement target portion in the state in which the Yb-axis direction conforms to or substantially conforms to the left-right direction of the target person P in the exercise state in which the target person P is sequentially carrying out the leaning motion and the returning motion and to relatively stably maintain the direction of the acceleration vector (including ↑As2) detected in the exercise state in the state in which the direction of the acceleration vector conforms to or substantially conforms to the direction that perpendicularly intersects the left-right direction of the target person P. Therefore, it is possible to cause the direction of the cross product vector ↑V calculated in STEP 14 for each measurement target portion to precisely conform to the Yb-axis direction in the body-side coordinate system CSb at each measurement target portion. Thus, it is possible to highly reliably identify the column vector (the vector of the second column) in the transformation matrix R(CSb→CSs) representing the Yb-axis direction in the body-side coordinate system CSb when seen in the sensor coordinate system CSs for each measurement target portion.

In addition, the coordinate axis direction estimation processing related to the coordinate axis Yb can be performed for all the measurement target portions by performing the leaning motion and the subsequent returning motion once in the embodiment.

Further, it is also possible to identify the column vector (the vector of the first column) in the transformation matrix R(CSb→CSs) representing the Xb-axis direction in the body-side coordinate system CSb when seen in the sensor coordinate system CSs with high reliability since the column vector (the vector of the first column) in the transformation matrix R(CSb→CSs) representing the Xb-axis direction in the body-side coordinate system CSb when seen in the sensor coordinate system CSs is obtained through the cross product operation from other two column vectors (the vectors of the second column and the third column) identified as described above for each measurement target portion.

Second Embodiment

Next, the second embodiment of the disclosure will be described with reference to FIGS. 7 to 9. Note that since the embodiment is different from the first embodiment only in a part of the coordinate axis direction estimation processing, description of matters that are the same as those in the first embodiment will be omitted.

In the first embodiment, the target person P stands up in the upright posture in order to estimate the Zb-axis direction in the body-side coordinate system CSb at each measurement target portion, and the target person P carries out the leaning motion and the returning motion in order to estimate the Yb-axis direction. Meanwhile, the embodiment is an embodiment in which directions of two coordinate axes in the body-side coordinate system CSb at each measurement target portion can be estimated in a state in which the target person P is seated in an object placed such that the target person P can be seated therein with the longitudinal direction of thighs of the respective legs being substantially horizontally aligned, for example, a chair Chr. Note that in the embodiment, the chair Chr is an example of an "object with a specific shape" according to the disclosure, and the state in which the target person P is seated in the chair Chr corresponds to the state in which the body of the target person P is in contact with the "object with a specific shape".

In the embodiment, coordinate axis direction estimation processing for the coordinate axis Zb in the body-side coordinate system CSb at each measurement target portion (an upper portion of the upper body, a waist portion, lower legs of the respective legs) other than the thighs of the respective legs among the measurement target portions of the target person P and the coordinate axis direction estimation processing for the coordinate axis Xb in the body-side coordinate system CSb (CSb(3)) at the thighs of the respective legs are performed as follows.

Figure 7:
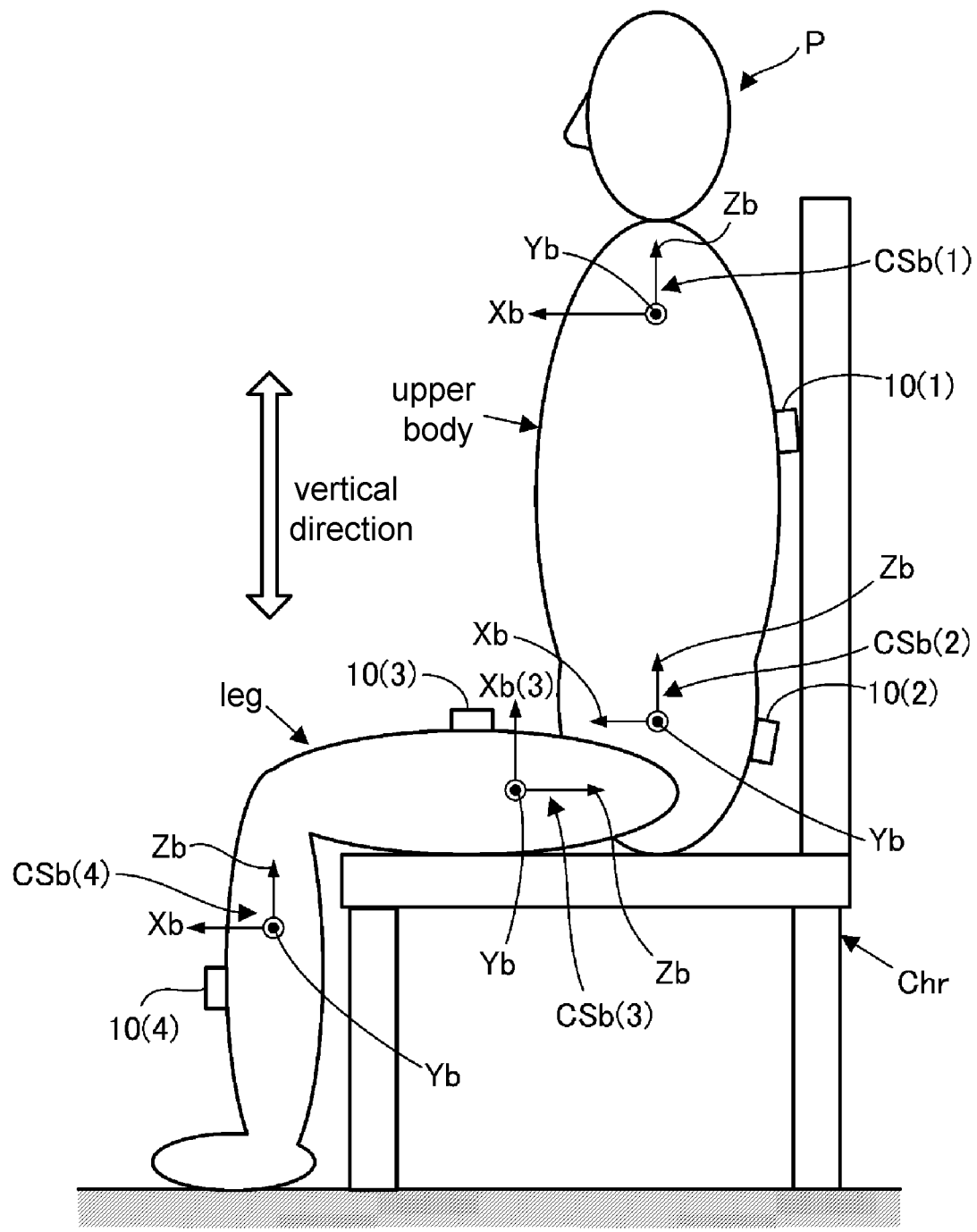
FIG. 7 is a diagram illustrating a seated state of a target person executed for processing for estimating a direction of a coordinate axis Zb or Xb in a body-side coordinate system CSb at a measurement target portion of a target person according to the second embodiment.

In the coordinate axis direction estimation processing, the target person P is kept still in a state in which the target person P is seated in the chair Chr such that the upper body and the lower legs of the respective legs are in an upright state in the vertical direction and the thighs of the respective legs extend in the horizontal direction on a seat surface of the chair Chr as illustrated in FIG. 7, for example. Note that at this time, the standing state of the upper body of the target person P may be assisted by an appropriate tool or a helper in order to minimize a force in the transverse direction acting on the upper body of the target person P.

The measurement processing device 20 executes the processing (the processing of detecting the accelerations using the acceleration sensor 12 in each inertial sensor 10) in STEP 1 and further executes the aforementioned processing in STEP 2 similarly to the first embodiment in the state in which the target person P is seated in the chair Chr in this manner, thereby calculating the average acceleration vector ↑As_ave for each measurement target portion.

Here, the Zb-axis direction in the body-side coordinate system CSb conforms to or substantially conforms to the vertical direction (gravity direction) for each measurement target portion other than the thighs of the respective legs of the target person P in the state in which the target person P is seated in the chair Chr as described above. Thus, the measurement processing device 20 identifies the element of the column (third column) corresponding to the Zb axis in the transformation matrix R(CSb→CSs) by executing the aforementioned processing in STEP 3 similarly to the first embodiment after the execution of the processing in STEP 2 for each measurement target portion other than the thighs of the respective legs of the target person P. In other words, the measurement processing device 20 calculates the vector (e13, e23, e33)$^T$ of the third column in the transformation matrix R (CSb→CSs) through the arithmetic operation processing of Equation (2a) or (2b) described above for each measurement target portion other than the thighs of the respective legs of the target person P.

Meanwhile, the Xb-axis direction in the body-side coordinate system CSb (CSb(3)) conforms to or substantially conforms to the vertical direction (gravity direction) for the thighs of the respective legs of the target person P in the state in which the target person P is seated in the chair Chr as described above. Thus, for the thighs of the respective legs of the target person P, the measurement processing device 20 identifies (estimates) an element of a column corresponding to the Xb axis in the transformation matrix R(CSb→CSs) on the assumption that the direction of the average acceleration vector ↑As_ave calculated in STEP 2 is the Xb-axis direction in the body-side coordinate system CSb (CSb(3)) at the thighs.

In this case, since the column corresponding to the Xb axis in the transformation matrix R(CSb→CSs) is the first column, the measurement processing device 20 calculates the vector (e11, e21, e31)$^T$ of the first column in the transformation matrix R(CSb→CSs) by transforming the average acceleration vector ↑As_ave calculated for the thighs into a unit vector as represented by Equations (4a) or (4b) below.

Note that which of Equations (4a) and (4b) is to be used to calculate the vector (e11, e21, e31)$^T$ of the first column depends on to which orientation of the directions of the respective coordinate axes the positive direction of each coordinate axis in each of the sensor coordinate system CSs and the body-side coordinate system CSb is set.

[Mathematical formula 4]

$$\begin{pmatrix} e11 \\ e21 \\ e31 \end{pmatrix} = \uparrow As\_ave / |\uparrow As\_ave| \quad (4a)$$

or $$\begin{pmatrix} e11 \\ e21 \\ e31 \end{pmatrix} = -\uparrow As\_ave / |\uparrow As\_ave| \quad (4b)$$

In the embodiment, the coordinate axis direction estimation processing for the coordinate axis Zb in the body-side coordinate system CSb at each measurement target portion (the upper portion of the upper body, the waist portion, and the lower legs of the respective legs) other than the thighs of the respective legs of the target person P and the coordinate axis direction estimation processing for the coordinate axis Xb in the body-side coordinate system CSb at each of the thighs of the legs are performed as described above.

Note that in the embodiment, the Zb-axis direction in the body-side coordinate system CSb at each measurement target portion other than the thighs of the respective legs of the target person P corresponds to the second direction according to the disclosure, and the vector (e13, e23, e33)$^T$ of the third column in the transformation matrix R(CSb→CSs) corresponds to the second posture data according to the disclosure. Also, the Xb-axis direction in the body-side coordinate system CSb at each of the thighs corresponds to the second direction according to the disclosure, and the vector (e11, e21, e31)$^T$ of the first column in the transformation matrix R(CSb→CSs) corresponds to the second posture data according to the disclosure, for the thighs of the respective legs.

Next, coordinate axis direction estimation processing for the coordinate axis Yb in the body-side coordinate system CSb at each measurement target portion (thighs and lower legs) of the respective legs of the target person P is performed as follows, for example. In other words, in the coordinate axis direction estimation processing, the target person P is kept still in a state in which the target person P is seated in the chair Chr (the state at the time t10) first such that the Yb-axis direction in the body-side coordinate system CSb (the left-right direction of the target person P) at each of the thigh and the lower leg of each leg corresponds to a direction (horizontal direction) that perpendicularly intersects the vertical direction as illustrated in FIG. 8. The kept-still state is a state before the target person P carries out the leg lifting motion and the left turning motion, which will be described later. Note that in the kept-still state, the lower leg of each leg and the upper body of the target person P may be inclined with respect to the vertical direction. Also, the thigh of each leg of the target person P may be inclined with respect to the horizontal direction.

In the state in which the target person P is seated and is kept still in the chair Chr as described above, the measurement processing device 20 executes the aforementioned processing in STEP 11 in the flowchart in FIG. 5 similarly to the first embodiment for each of the thigh and the lower leg of each leg. In this manner, the acceleration vector detected by the acceleration sensor 12 in the inertial sensor 10 (the acceleration vector in the vertical direction caused by the gravity) is set as the reference acceleration vector ↑As1 for each of the thigh and the lower leg of each leg.

Note that an average acceleration vector ↑As_ave obtained through the aforementioned processing in STEPS 1 and 2 in FIG. 3, for example, may be set as the reference acceleration vector ↑As1 for each of the thigh and the lower leg of each leg in the state in which the target person P is seated and kept still in the chair Chr.

Figure 8:
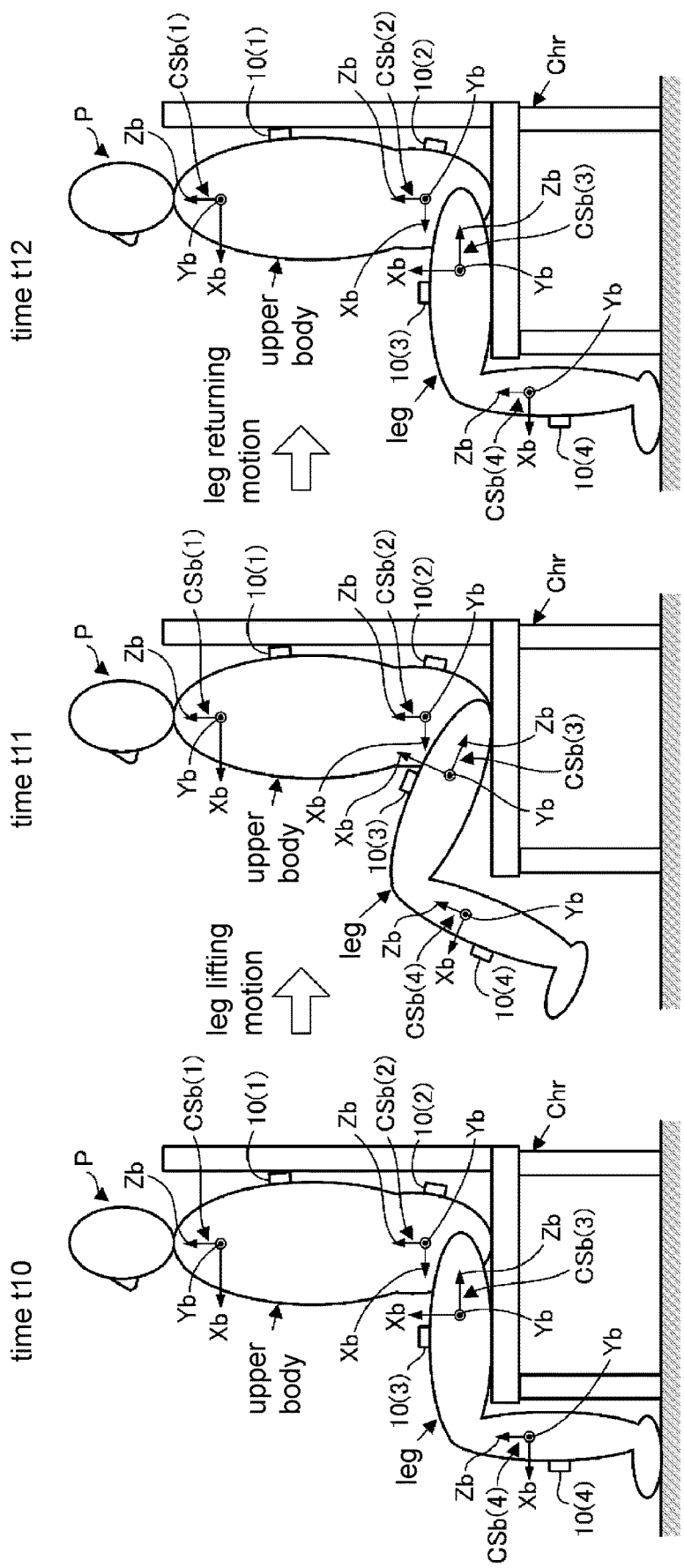
FIG. 8 is a diagram illustrating an operation executed by the target person for processing for estimating a direction of a coordinate axis Yb in the body-side coordinate system CSb at a measurement target portion on a leg of the target person according to the second embodiment.
Figure 9:
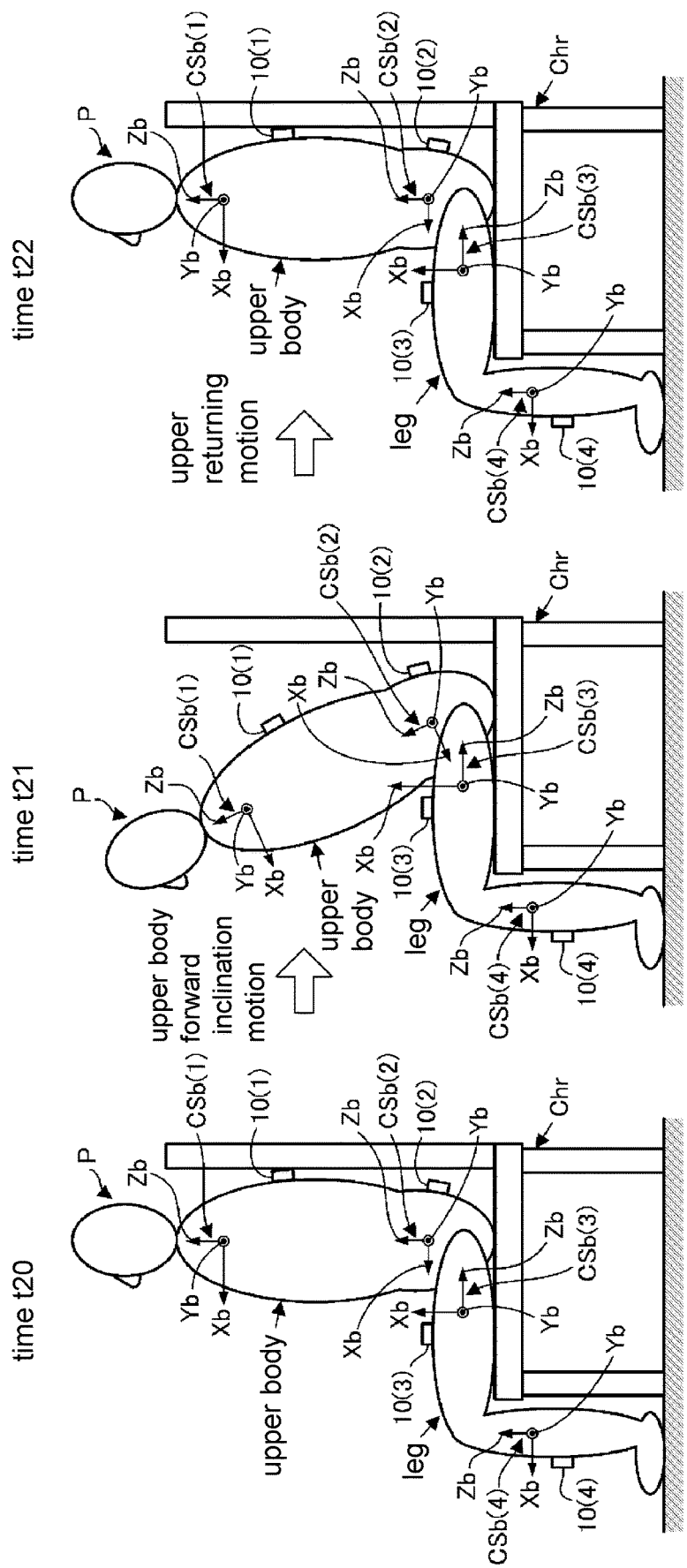
FIG. 9 is a diagram illustrating an operation executed by the target person for processing for estimating the direction of the coordinate axis Yb in the body-side coordinate system CSb at a measurement target portion on an upper body of the target person according to the second embodiment.

Next, the target person P carries out a leg lifting motion in which both legs are lifted while rotating the legs in the pitch direction at hip joints from the kept-still state in STEP 11 as illustrated in FIG. 8 (the state at the time t10) as illustrated in FIG. 9 and then carries out a leg returning motion in which both the legs are lowered and returned to the original state (the state at the time t12) from the state in which both the legs are lifted through the leg lifting motion (the state at the time t11) through a motion opposite to the leg lifting motion (a motion in the pitch direction) in the coordinate axis direction estimation processing. Note that the leg lifting motion and the leg returning motion of the target person P may be assisted by an appropriate tool, a helper, or the like. Also, these motions of the target person P may be carried out slowly.

The measurement processing device 20 executes the aforementioned processing in STEP 12 to 15 in the flowchart illustrated in FIG. 5 similarly to the first embodiment for each of the thighs and the lower legs of the respective legs in parallel to such a motion of the respective legs carried out by the target person P. Note that in this case, the switching timing detected in STEP 13 is a timing at which the leg lifting motion of each leg is switched to the leg returning motion.

In this case, the direction of the acceleration vector that occurs in the inertial sensor 10 at each of the thigh and the lower leg of each leg is maintained in a state in which the direction of the acceleration vector conforms to or substantially conforms to the direction that perpendicularly intersects the left-right direction of the target person P in the state in which the target person P is carrying out the leg lifting motion and the leg returning motion. Thus, the direction of the cross product vector ↑V calculated in STEP 14 conforms to or substantially conforms to the Yb-axis direction in the body-side coordinate system CSb for each of the thigh and the lower leg of each leg. Therefore, it is possible to appropriately identify(estimate) the element of the column corresponding to the Yb axis in the transformation matrix R(CSb→CSs) by executing the processing illustrated in the flowchart in FIG. 5.

Next, coordinate axis direction estimation processing for the coordinate axis Yb in the body-side coordinate system CSb at the measurement target portion (the upper portion of the upper body and the waist portion) of the upper body of the target person P is performed as follows, for example. In other words, in the coordinate axis direction estimation processing, the target person P is kept still in a state in which the target person P is seated in the chair Chr (the state at the time t20) such that the Yb-axis direction (the left-right direction of the target person P) in the body-side coordinate system CSb at each of the upper portion of the upper body and the waist portion corresponds to the direction (horizontal direction) that perpendicularly intersects the vertical direction as illustrated in FIG. 9 first. The kept-still state is a state before the target person P carries out an upper body forward inclination motion and an upper body returning motion, which will be described later. Note that in the kept-still state, the lower legs of the respective legs and the upper body of the target person P may be inclined with respect to the vertical direction similarly to the kept-still state before starting the leg lifting motion. Also, the thighs of the respective legs of the target person P may be inclined with respect to the horizontal direction.

In the state in which the target person P is seated and kept still in the chair Chr as described above, the measurement processing device 20 executes the aforementioned processing in STEP 11 in the flowchart in FIG. 5 similarly to the first embodiment for each of the upper portion of the upper body and the waist portion of the target person P. In this manner, the acceleration vector (the acceleration vector in the vertical direction caused by the gravity) detected by the acceleration sensor 12 in the inertial sensor 10 as the reference acceleration vector ↑As1 for each of the upper portion of the upper body and the waist portion.

Note that an average acceleration vector ↑As_ave obtained through the aforementioned processing in STEPS 1 and 2 in FIG. 3, for example, may be set as the reference acceleration vector ↑As1 for each of the upper portion of the upper body and the waist portion in the state in which the target person P is seated and kept still in the chair Chr.

Next, the target person P carries out an upper body forward inclination motion in which the upper body is inclined forward in the pitch direction from the kept-still state in STEP 11 (the state at the time t20) as illustrated in FIG. 9 and then carries out an upper body returning motion in which the upper body is inclined backward in the pitch direction to return the upper body to the original state (the state at the time t22) from the state in which the upper body is inclined forward through the upper body forward inclination motion (the state at the time t21) in the coordinate axis direction estimation processing. Note that in this case, the upper body forward inclination motion and the upper body returning motion of the target person P may be assisted by an appropriate tool, a helper or the like. In addition, these motions of the target person P may be carried out slowly.

The measurement processing device 20 executes the aforementioned processing illustrated in STEPS 12 to 15 in the flowchart in FIG. 5 similarly to the first embodiment for each of the upper portion of the upper body and the waist portion in parallel to the exercise of the upper body carried out by the target person P. Note that in this case, the switching timing detected in STEP 13 is a timing at which the upper body forward inclination motion is switched to the upper body returning motion.

In this case, the direction of the acceleration vector that occurs in the inertial sensor 10 at each of the upper portion of the upper body and the waist portion is kept substantially constant in a state in which the direction of the acceleration vector conforms to or substantially conforms to a direction that perpendicularly intersects the left-right direction of the target person P in the state in which the target person P is carrying out the upper body forward inclination motion and the upper body returning motion. The direction of the cross product vector ↑V calculated in STEP 14 thus conforms to or substantially conforms to the Yb-axis direction in the body-side coordinate system CSb for each of the thighs and the lower legs of the respective legs. Therefore, it is possible to appropriately identify (estimate) the element of the column corresponding to the Yb axis in the transformation matrix R(CSb→CSs) by executing the processing illustrated in the flowchart in FIG. 5.

Note that the target person P may carry out the leg lifting motion and the upper body forward inclination motion in parallel and may also carry out the leg returning motion and the upper body returning motion in parallel. In this case, it is possible to carry out the processing illustrated in the flowchart in FIG. 5 in parallel for each of the measurement target portions at the thighs and the lower legs of the respective legs and the upper portion of the upper body and the waist portion.

Also, in the embodiment, the Yb-axis direction in the body-side coordinate system CSb at each measurement target portion of the target person P corresponds to the first direction according to the disclosure, and the vector (e12, e22, e32)$^T$ of the second column in the transformation matrix R(CSb→CSs) corresponds to the first posture data according to the disclosure.

Next, coordinate axis direction estimation processing for the coordinate axis Xb in the body-side coordinate system CSb at each measurement target portion (the upper portion of the upper body, the waist portion, and the lower legs of the respective legs) other than the thighs of the respective legs of the target person P and coordinate axis direction estimation processing for the coordinate axis Zb in the body-side coordinate system CSb (CSb(3)) at the thighs of the respective legs are performed as follows.

That is, the measurement processing device 20 calculates the vector (e11, e21, e31)$^T$ of the first column corresponding to the Xb axis through a cross product operation (an arithmetic operation of a vector product) between the vector (e12, e22, e32)$^T$ of the second column corresponding to the Yb axis and the vector (e13, e23, e33)$^T$ of the third column corresponding to the Zb axis in the body-side coordinate system CSb at each measurement target portion similarly to the first embodiment in the coordinate axis direction estimation processing for the coordinate axis Xb in the body-side coordinate system CSb at each measurement target portion (the upper portion of the upper body, the waist portion, and the lower legs of the respective legs) other than the thighs of the respective legs of the target person P. In this manner, the Xb-axis direction (the direction when seen in the sensor coordinate system CSs) in the body-side coordinate system CSb at each measurement target portion other than the thighs of the respective legs of the target person P is identified.

Meanwhile, the measurement processing device 20 obtains the vector $(e13, e23, e33)^T$ of the third column corresponding to the Zb-axis element in the transformation matrix R(CSb→CSs) as a unit vector that perpendicularly intersects the vector $(e11, e21, e31)^T$ of the first column obtained as described above for the thigh and the vector $(e12, e22, e32)^T$ of the second column for the thigh of each leg of the target person P. Specifically, the vector $(e13, e23, e33)^T$ of the third column is calculated by the cross product operation (the arithmetic operation of the vector product) of the vector $(e11, e21, e31)^T$ of the first column and the vector $(e12, e22, e32)^T$ of the second column.

Note that in the embodiment, the Xb-axis direction in the body-side coordinate system CSb at each measurement target portion other than the thighs of the respective legs of the target person P corresponds to the third direction according to the disclosure, and the vector $(e11, e21, e31)^T$ of the first column in the transformation matrix R(CSb→CSs) corresponds to the third posture data according to the disclosure. Also, the Zb-axis direction in the body-side coordinate system CSb at each thigh corresponds to the third direction according to the disclosure, and the vector $(e13, e23, e33)^T$ of the third column in the transformation matrix R(CSb→CSs) corresponds to the third posture data according to the disclosure for the thigh of each leg.

In the embodiment, the element of each column in the transformation matrix R(CSb→CSs) is obtained for each measurement target portion as described above. In this manner, the relative posture relationship between the sensor coordinate system CSs and the body-side coordinate system CSs (in other words, the relative posture relationship between the inertial sensor 10 and the measurement target portion) is identified (estimated) by the transformation matrix R(CSb→CSs) for each measurement target portion similarly to the first embodiment.

In this case, the coordinate axis direction estimation processing related to the coordinate axis Zb in the body-side coordinate system CSb at each measurement target portion other than the thighs of the respective legs of the target person P and the coordinate axis direction estimation processing related to the coordinate axis Xb in the body-side coordinate system CSb of the thigh of each leg are performed using the acceleration detection data in the state in which the target person P is seated in the chair Chr as illustrated in FIG. 7. In addition, in the state in which the target person P is seated in this manner, it is possible to relatively stably maintain the Zb-axis direction in the body-side coordinate system CSb at each measurement target portion other than the thighs of the respective legs and the Xb-axis direction in the body-side coordinate system CSb at the thigh of each leg in a state in which the Zb-axis direction and the Xb-axis direction conforms to or substantially conforms to the vertical direction (gravity direction).

Therefore, it is possible to highly reliably identify the column vector (the vector of the third column) in the transformation matrix R(CSb→CSs) representing the Zb-axis direction in the body-side coordinate system CSb when seen in the sensor coordinate system CSs for each measurement target portion other than the thighs of the respective legs. Also, it is possible to highly reliably identify the column vector (the vector of the first column) in the transformation matrix R(CSb→CSs) representing the Xb-axis direction in the body-sie coordinate system CSb when seen in the sensor coordinate system CSs for the thighs of the respective legs.

Also, coordinate axis direction estimation processing related to the coordinate axis Yb in the body-side coordinate system CSb when seen in the sensor coordinate system CSs at each of the thigh and the lower leg of each leg among the measurement target portions is performed using the reference acceleration vector ↑As1 detected in the state in which the target person P is seated and kept still in the chair Chr and acceleration vector ↑As2 detected at a predetermined timing in the state in which the target person P is sequentially carrying out the leg lifting motion and the leg returning motion (a switching timing from the leg lifting motion to the leg returning motion in the embodiment) or the acceleration vector ↑As2 detected at a predetermined timing in the state in which the target person P is sequentially carrying out the upper body forward inclination motion and the upper body returning motion (a switching timing from the upper body forward inclination motion to the upper body returning motion in the embodiment).

In this case, the reference acceleration vector ↑As1 detected in the state in which the target person P is seated and kept still in the chair Chr precisely becomes a vector in the vertical direction (the vector that perpendicularly intersects the left-right direction of the target person P). Also, in the exercise state in which the target person P sequentially carries out the leg lifting motion and the leg returning motion, it is possible to relatively stably maintain the Yb-axis direction in the body-side coordinate system CSb at each of the thigh and the lower leg of each leg in a state in which the Yb-axis direction conforms to or substantially conforms to the left-right direction of the target person P and to relatively stably maintain the direction of the acceleration vector (including ↑As2) detected in the exercise state in a state in which the direction of the acceleration vector conforms to or substantially conforms to the direction that perpendicularly intersects the left-right direction of the target person P.

Similarly, in the exercise state in which the target person P sequentially carries out the upper body forward inclination motion and the upper body returning motion, it is possible to relatively stably maintain the Yb-axis direction in the body-side coordinate system CSb at each of the upper portion of the upper body and the waist portion in a state in which the Yb-axis direction conforms to or substantially conforms to the left-right direction of the target person P and to relatively stably maintain the direction of the acceleration vector (including ↑As2) detected in the exercise state in a state in which the direction of the acceleration vector conforms to or substantially conforms to the direction that perpendicularly intersects the left-right direction of the target person P.

Therefore, it is possible to cause the direction of the cross product vector ↑V calculated in STEP 14 described above for each measurement target portion to precisely conforms to the Yb-axis direction in the body-side coordinate system CSb for each measurement target portion similarly to the first embodiment. Thus, it is possible to highly reliably identify the column vector (the vector of the second column) in the transformation matrix R(CSb→CSs) representing the Yb-axis direction in the body-side coordinate system CSb when seen in the sensor coordinate system CSs for each measurement target portion.

Further, the column vector (the vector of the first column) in the transformation matrix R(CSb→CSs) representing the Xb-axis direction in the body-side coordinate system CSb when seen in the sensor coordinate system CSs for each measurement target portion other than the thighs of the respective legs of the target person P is obtained through the cross product operation from other two column vectors (the vectors of the second column and the third column) identified as described above. Therefore, it is also possible to highly reliably identify the column vector (the vector of the first column) in the transformation matrix R(CSb→CSs) representing the Xb-axis direction in the body-side coordinate system CSb when seen in the sensor coordinate system CSs for each measurement target portion other than the thighs of the respective legs of the target person P.

Also, the column vector (the vector of the third column) in the transformation matrix R(CSb→CSs) representing the Zb-axis direction in the body-side coordinate system CSb when seen in the sensor coordinate system CSs for the thigh of each leg of the target person P is obtained through a cross product operation from other two column vectors (the vectors of the first column and the second column) identified as described above. Therefore, it is possible to highly reliably identify the column vector (the vector of the third column) in the transformation matrix R(CSb→CSs) representing the Zb-axis direction in the body-side coordinate system CSb when seen in the sensor coordinate system CSs for the thigh of each leg of the target person P.

Further, it is possible to acquire the acceleration detection data used in the coordinate axis direction estimation processing in the seated state of the target person P in the embodiment and thereby to easily apply the detection data to a target person P, for whom it is difficult to be in the upright posture state (for example, a child, a person with weak leg strength, or the like).

Note that the disclosure is not limited to the aforementioned first embodiment or the second embodiment and other embodiments can also be employed. Hereinafter, some of other embodiments will be described.

In the respective embodiments, the acceleration vector ↑As2 that has a direction that is different from the direction of the reference acceleration vector ↑As1 detected in the state in which the target person P is kept still is detected using the inertial sensor 10 at each measurement target portion when the target person P is carrying out exercise of causing the posture of the measurement target portion at each of the upper body and the legs of the target person P to change in the pitch direction for each measurement target portion, and the direction of the coordinate axis Yb (the coordinate axis in the left-right direction) at each measurement target portion when seen in the sensor coordinate system CSs is identified using the acceleration vector ↑As2 and the reference acceleration vector ↑As1.

Instead, the acceleration vector ↑As2 that has a direction that is different from the direction of the reference acceleration vector ↑As1 detected in the state in which the target person P is kept still in the pitch direction is detected with the inertial sensor 10 at each measurement target portion for each measurement target portion when the target person P is carrying out exercise of causing the posture of the measurement target portion at each of the upper body and the legs of the target person P to change in the rolling direction (the direction around the axis in the front-back direction of the target person P), and the direction of the coordinate axis Xb may be identified by regarding the direction of the cross product vector between the acceleration vector ↑As2 and the reference acceleration vector ↑As1 as the direction of the coordinate axis Xb (the coordinate axis in the front-back direction) at each measurement target portion when seen in the sensor coordinate system CSs.

In this case, exercise of causing the upper body to be inclined leftward and rightward, a motion of swinging the respective legs on the left side or the right side around the hip joint, or the like can be employed, for example, as the motion in the rolling direction. Also, in this case, the Yb-axis direction at each measurement target portion may be identified through the cross product operation between the vector of the third column (this can be identified similarly to the aforementioned respective embodiments) representing the Zb-axis direction in the transformation matrix R(CSb→CSs) and the vector of the first column representing the Xb-axis direction.

In addition, the motion of the target person P from which the acceleration vector ↑As2 is detected for identifying the Yb-axis direction at each measurement target portion may be performed individually for each measurement target portion.

Also, the acceleration vector detected at the motion switching timing of the target person P is used as the acceleration vector ↑As2 that has a direction that is different from the direction of the reference acceleration vector ↑As1 (the acceleration vector caused by the gravity) at each measurement target portion in the pitch direction in the embodiments.

The acceleration vector ↑As2 acquired when the target person P is carrying out the exercise may be an acceleration vector detected at another time around the switching timing, for example. Further, acceleration vectors may be detected at a plurality of sampling times during a period near the switching timing, for example, (or a period during which the direction of the acceleration vector that occurs in the inertial sensor 10 changes into a direction that is different from the direction of the reference acceleration vector ↑As1) for each measurement target portion, cross product vectors between each of the plurality of acceleration vectors and the reference acceleration vector ↑As1 may be obtained, and a direction obtained by averaging the directions of the plurality of cross product vectors may be identified as the Yb-axis direction in the body-side coordinate system CSb when the target person P is carrying out the exercise. Alternatively, the direction of an eigenvector of a first main element obtained through main element analysis processing may be identified as the Yb-axis direction in the body-side coordinate system CSb from the plurality of cross product vectors, for example.

The method of identifying the Yb-axis direction as described above is similarly applied to a case in which the acceleration vector ↑As2 is detected when exercise in a rolling direction at a measurement target portion is carried out and the Xb-axis direction is identified using the acceleration vector ↑As2 and the reference acceleration vector ↑As1.

Also, the measurement target portions are not limited to the upper body or the respective legs of the target person P, and measurement target portions may be set at arms of the target person P, for example. In this case, it is possible to identify the coordinate axis direction of the upward-downward direction (longitudinal direction) of the arms from acceleration detection data in a state in which the target person P let his/her arms with the measurement target portions drop downward, for example. Also, it is possible to identify the coordinate axis direction in the left-right direction of the arms from the acceleration vector detected during execution of a motion of swinging the arms with the measurement target portion forward or backward in the pitch direction around shoulder joints and the acceleration vector (reference acceleration vector) detected in the kept-still state before starting the exercise, for example. In addition, it is possible to identify the coordinate axis direction in the front-back direction of the arms from the acceleration vector detected during execution of exercise of swinging the arms with the measurement target portions rightward or leftward in the rolling direction around the shoulder joints and the acceleration vector (reference acceleration vector) detected in the kept-still state before starting the exercise, for example.

Also, although the inertial sensor 10 is a sensor including the angular speed sensor 11 and the acceleration sensor 12 in the aforementioned respective embodiments, the inertial sensor 10 may be a sensor that does not include the angular speed sensor 11.

In addition, the coordinate axis direction estimation processing for one coordinate axis in the body coordinate system Cb at a measurement target portion is executed with the coordinate axis directed in the vertical direction in the state in which the target person P is seated and kept still in the chair Chr in the aforementioned second embodiment. However, in order to enable the one coordinate axis in the body coordinate system Cb at the measurement target portion to be directed in the vertical direction and kept still, an appropriate portion of the body of the target person P may be caused to abut on another object (an object with a specific shape) other than the chair Chr, and the coordinate axis direction estimation processing for the one coordinate axis (the coordinate axis directed in the vertical direction) in the body coordinate system Cb at the measurement target portion may be executed in this state.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A method for estimating an attachment posture of an inertial sensor, for estimating a relative posture relationship between a measurement target portion of a target person by a measurement processing device and an inertial sensor that is attached to the measurement target portion and includes an acceleration sensor capable of communicating with the measurement processing device and detecting accelerations in the respective coordinate axes in a sensor coordinate system, which is a three-dimensional coordinate system set in advance for the inertial sensor, the method for estimating an attachment posture of an inertial sensor comprising:

a first process of detecting, with the acceleration sensor, a first acceleration vector that is an acceleration vector including a set of accelerations in three coordinate axis directions in the sensor coordinate system in a state in which the measurement target portion is kept still, and maintaining a first direction which is a predetermined direction set in advance with respect to the measurement target portion in a direction that perpendicularly intersects a vertical direction;

a second process of allowing the target person to carry out exercise of causing a posture of the measurement target portion to change in a direction around an axis in the first direction with the first direction of the measurement target portion maintained in a direction that is the same as the direction in the first process;

a third process of detecting, with the acceleration sensor, a second acceleration vector that is an acceleration vector including a set of accelerations in the three coordinate axis directions in the sensor coordinate system and has a direction that is different from a direction of the first acceleration vector, at one or more sampling times in the second process;

a fourth process of identifying first posture data by the measurement processing device that indicates which direction in the sensor coordinate system the first direction of the measurement target portion corresponds to when seen in the sensor coordinate system, on the basis of one or more cross product vectors calculated in a cross product operation between each of one or more second acceleration vectors detected in the third process and the first acceleration vector detected in the first process;

a fifth process of allowing the target person to keep the measurement target portion still such that a second direction that is set in advance with respect to the measurement target portion as a direction that is different from the first direction is maintained in a vertical direction;

a sixth process of detecting, with the acceleration sensor, a set of accelerations of the three coordinate axis directions in the sensor coordinate system at one or more sampling times in the fifth process;

a seventh process of identifying second posture data indicating which direction in the sensor coordinate system the second direction of the measurement target portion corresponds to, on the basis of one or more sets of accelerations detected in the fifth process; and an eighth process of identifying third posture data indicating which direction a third direction that perpendicularly intersects the first direction and the second direction corresponds to when seen in the sensor coordinate system on the basis of the first posture data identified in the fourth process and the second posture data identified in the seventh process, wherein in the eighth process, a vector obtained through a cross product operation of a vector in the first direction indicated by the first posture data and a vector in the second direction indicated by the second posture data is identified as the third posture data.

2. The method for estimating an attachment posture of an inertial sensor according to claim 1, wherein the exercise that the target person is allowed to carry out in the second process is exercise of sequentially causing the posture of the measurement target portion to change in one of a forward direction and a reverse direction that is a direction around the axis in the first direction and causing the posture of the measurement target portion to change in the other direction, and the second acceleration vector detected in the third process includes at least an acceleration vector at a timing of switching of a direction of a change in posture of the measurement target portion around the axis in the first direction.

3. The method for estimating an attachment posture of an inertial sensor according to claim 2, wherein the measurement target portion is lower legs or thighs of legs of the target person, the first direction is a left-right direction of the target person, and the exercise that the target person is allowed to carry out in the second process is exercise that includes at least bending and stretching the legs such that a posture of the thighs or the lower legs of the legs is caused to change in a pitch direction.

4. The method for estimating an attachment posture of an inertial sensor according to claim 2,
wherein the measurement target portion is an upper body of the target person,
the first direction is a left-right direction of the target person, and
the exerciser that the target person is allowed to carry out in the second process is exercise that includes at least inclining the upper body of the target person in a pitch direction.

5. The method for estimating an attachment posture of an inertial sensor according to claim 1,
wherein the measurement target portion is lower legs or thighs of legs of the target person,
the first direction is a left-right direction of the target person, and
the exercise that the target person is allowed to carry out in the second process is exercise that includes at least bending and stretching the legs such that a posture of the thighs or the lower legs of the legs is caused to change in a pitch direction.

6. The method for estimating an attachment posture of an inertial sensor according to claim 1,
wherein the measurement target portion is an upper body of the target person,
the first direction is a left-right direction of the target person, and
the exerciser that the target person is allowed to carry out in the second process is exercise that includes at least inclining the upper body of the target person in a pitch direction.

7. The method for estimating an attachment posture of an inertial sensor according to claim 1,
wherein the measurement target portion is a lower leg or a thigh of a leg or an upper body of the target person, and
the second direction is a direction that is able to be directed in the vertical direction in a state in which the target person is standing up in an upright posture or in a state in which a body of the target person is kept still in contact with an object with a specific shape.

* * * * *